United States Patent
Bauch et al.

(10) Patent No.: US 10,457,559 B2
(45) Date of Patent: Oct. 29, 2019

(54) METHOD FOR PURIFYING HALOGENATED OLIGOSILANES

(71) Applicant: PSC POLYSILANE CHEMICALS GMBH, Bitterfeld-Wolfen (DE)

(72) Inventors: Christian Bauch, Muldestausee-Ot Muldenstein (DE); Sven Holl, Gückingen (DE); Matthias Heuer, Sandersdorf-Brehna Ot Ramsin (DE)

(73) Assignee: PSC POLYSILANE CHEMICALS GMBH, Bitterfeld-Wolfen (DE)

( * ) Notice: Subject to any disclaimer, the term of this patent is extended or adjusted under 35 U.S.C. 154(b) by 49 days.

(21) Appl. No.: 15/508,312

(22) PCT Filed: Sep. 7, 2015

(86) PCT No.: PCT/DE2015/000439
§ 371 (c)(1),
(2) Date: Mar. 2, 2017

(87) PCT Pub. No.: WO2016/037601
PCT Pub. Date: Mar. 17, 2016

(65) Prior Publication Data
US 2017/0247260 A1    Aug. 31, 2017

(30) Foreign Application Priority Data
Sep. 8, 2014  (DE) .......................... 10 2014 013 250

(51) Int. Cl.
C01B 33/107   (2006.01)
C01B 33/04    (2006.01)
B01D 3/34     (2006.01)
C01B 33/00    (2006.01)
C07F 7/20     (2006.01)
C07D 323/00   (2006.01)
C08G 77/60    (2006.01)
C08K 3/16     (2006.01)
C08K 5/54     (2006.01)

(52) U.S. Cl.
CPC .......... *C01B 33/10773* (2013.01); *B01D 3/34* (2013.01); *C01B 33/00* (2013.01); *C01B 33/04* (2013.01); *C01B 33/10778* (2013.01); *C07D 323/00* (2013.01); *C07F 7/20* (2013.01); *C08G 77/60* (2013.01); *C08K 3/16* (2013.01); *C08K 5/54* (2013.01)

(58) Field of Classification Search
CPC ................... C01B 33/10773; C01B 33/10778
See application file for complete search history.

(56) References Cited

U.S. PATENT DOCUMENTS

| 2,877,097 | A | 3/1959 | Wolff |
| 3,414,603 | A | 12/1968 | Mlavski |
| 4,224,040 | A | 9/1980 | Gazzarrini et al. |
| 4,390,510 | A | 6/1983 | Ritzer |
| 4,676,967 | A | 6/1987 | Breneman |
| 4,713,230 | A | 12/1987 | Doornbos |
| 4,985,579 | A | 1/1991 | Bokerman et al. |
| 2004/0028594 | A1* | 2/2004 | Klein ................ C01B 33/10778 423/342 |
| 2005/0054211 | A1 | 3/2005 | Xu et al. |
| 2010/0266489 | A1* | 10/2010 | Rauleder ............... C01B 33/046 423/700 |
| 2011/0184205 | A1 | 7/2011 | Rauleder |
| 2013/0270102 | A1 | 10/2013 | Auner et al. |

FOREIGN PATENT DOCUMENTS

| DE | 28 52 598 | 6/1979 |
| DE | 100 57 482 | 5/2002 |
| DE | 10 2007 050 199 | 4/2009 |
| DE | 10 2009 027 729 | 1/2011 |
| JP | 5 61 971 29 | 5/1986 |
| JP | 2001002407 A * | 1/2001 |
| WO | WO 2011/006695 | 1/2011 |
| WO | WO 2012/001180 | 7/2011 |
| WO | WO 2016/037601 | 3/2016 |

OTHER PUBLICATIONS

One printed page from web-site vol. 3, dated May 5, 1964 Author: Charles H.. Van Dyke and Alan G. MacDiarmid Title of article: The Reaction of 1,2-Disilyldisiloxane, 1-Silyldisiloxane, and 1,1, 1-Trimethyldisiloxane with Boron Trichloride Contribution from the: John Harrison Laboratory of Chemistry, and University of Pennsylvania, Philadelphia 4, PA.

* cited by examiner

Primary Examiner — Ngoc-Yen Nguyen
(74) Attorney, Agent, or Firm — Horst M. Kasper, Esq.

(57) ABSTRACT

The invention relates to a method for purifying halogenated oligosilanes in the form of a pure compound or a mixture of compounds with respectively at least one direct Si—Si bond, the substituents thereof being exclusively made from halogen or from halogen and hydrogen and in the composition thereof, the atomic ratio of the substituents:silicon is at least 3:2, by the action of at least one purification agent on the halogenated oligosilane and by isolating the halogenated oligosilanes with improved purity. According to prior art, halogenated monosilanes such as $HSiCl_3$ are purified by treating with organic compounds, preferably polymers, containing amino groups, and are separated from said mixtures. Based on the contained amino groups, said method can not be used for halogenated oligosilanes as the secondary reactions lead to a decomposition of the products. The novel method is used to provide the desired products in a high yield and purity without using the amino groups.

16 Claims, No Drawings

METHOD FOR PURIFYING HALOGENATED OLIGOSILANES

The present invention relates to a method for the purification of halogenated oligosilanes as a pure compound or mixture of compounds each having at least one direct Si—Si bond, the substituents thereof being exclusively halogen or halogen and hydrogen, and the composition thereof being a substituent:silicon atom ratio of at least 3:2.

PRIOR ART

Other methods for the removal of specific contaminants from halogenated silanes are known from the prior art:

A method for reducing contamination in silanes due to metallic compounds or metalloid elements is disclosed in DE102009027729, in which organic compounds that contain amino groups are added to the corresponding silanes as scavenger reagents. These amino groups function as ligands and coordinate to the metal or metalloid centers. In addition to metal compounds such as iron chlorides, boron compounds can also be removed in this way.

Van Dyke, et al., (Inorg. Chem., Vol. 3, No. 5, 1964, pp 747-752) describe the reaction of boron trichloride with various silyl siloxanes, wherein these are cleaved to silyl chlorides.

DISADVANTAGES OF THE PRIOR ART

The method presented in DE102009027729 A1 is not suitable for purifying halogenated oligosilanes because this method requires the addition of organic compounds having amino groups to the product mixtures. Such reagents cannot be used in the case of oligosilanes because it is known that amino groups cause skeletal rearrangements in halogenated oligosilanes, wherein shorter-chain halosilanes on the one hand, e.g., SiC, and longer-chain highly branched halosilanes on the other hand, e.g., $(SiCl_3)_4Si$, can arise.

This can result in the complete decomposition of the desired product; therefore, this method cannot be used with halogenated oligosilanes.

The method of Van Dyke, et al., only relates to the removal of various siloxanes, but not the reduction of a contamination due to metallic compounds or metalloid elements.

Moreover, the addition of $BCl_3$ to the product mixture is necessary to this end, which rules out many applications of the halogenated oligosilanes because, e.g., in semiconductor manufacturing, wherein boron is a critical element since it acts as a dopant.

TABLE 1

Abbreviations and synonyms

| Abbreviations | |
|---|---|
| Reactants | Starting materials for a chemical reaction |
| Precursors | Raw materials for the respective process in question |
| 18-crown-6 | Cyclic polyether with 18 ring atoms (6 of which are oxygen) |
| OCS | Chlorinated oligosilanes |
| Siloxanyl | O-SiR$_3$ (R = halogen and/or H and/or organyl/siloxanyl) |
| Si$_2$Cl$_6$ | Hexachlorodisilane (HCDS) |
| Si$_2$Cl$_6$O | Hexachlorodisiloxane (HCDSO) |
| ppm = ppmw | Parts per million by weight ($10^{-6}$) |
| ppb = ppbw | Parts per billion by weight ($10^{-9}$) |
| HCl | Hydrogen chloride gas |
| hPa | Hectopascal = 1 mbar |

OBJECT

The aim is to provide a method for purifying halogenated oligosilanes that will safely and quickly remove trace contaminants from the product, especially metal-containing compounds, with low material and cost expenditures and without significantly reducing the OCS product yields. The purity can hereby be increased, particularly in terms of contamination by dopants and metal compounds and other elements detrimental to applications in the semiconductor industry.

Solution to Problems in the Prior Art

This object is attained through the features listed in claim 1 for the method for purifying halogenated oligosilanes $Si_nX_{2n+2}$ with n=2 through n=6 as pure compounds or as mixtures of compounds in which the substituents X comprise chlorine or chlorine and hydrogen, characterized in that
1. a fluoride is added to the halogenated oligosilane, wherein said fluoride is in pure form and/or as a fluoride mixture and/or as a fluorine-containing compound and/or preparation and added in an amount, when calculated as F$^-$ in relation to the mass of the halogenated oligosilane, of more than 1 ppb, preferably more than 100 ppb, especially preferably more than 1 ppm, especially more than 10 ppm,
2. at least one processing phase takes place in which at least the fluoride acts upon the halogenated oligosilane, wherein the at least one processing is selected from a group comprising stirring, swirling, shaking, heating to reflux, diffusing, and passing through, preferably at least two processing phases comprising stirring and heating to reflux,
3. at least one separation method for the isolation of the halogenated oligosilane takes place, selected from a group comprising decanting, filtering, distilling, and subliming,
4. and the halogenated oligosilane exhibits a reduced metal content after the purification.

The advantages achieved by the method of the present invention for purifying chlorinated oligosilanes consist in particular in contaminants being selectively bound using a purification agent, while the prior art requires very lengthy and expensive distillation steps to achieve the purity needed for the semiconductor industry.

An advantageous embodiment is given by Claim 2:

Method according to claim 1, characterized in that the fluoride is selected from a group comprising alkali metal fluorides, alkaline earth metal fluorides, silicon fluorides $Si_nX_oF_p$ (X=halogen, organyl, siloxanyl and/or hydrogen; o+p=2n+2; n ≥1), and zinc fluoride, preferably alkali metal fluorides, especially preferably potassium fluoride.

The fluoride used should be inexpensive and should be easily removable again in the planned separation process. Furthermore, the respective additional components such as counterions should not enter into any undesired reactions with the OCS, which, for example, is the case with potassium fluoride.

One skilled in the art will readily recognize that many compounds can be considered in the choice of fluoride, while it is essentially only important that the specific compound fluoride (F$^-$) can be made available for the reaction. Therefore, other fluorides can re-place those mentioned here in whole or in part, without losing the essence of the method of the present invention.

Another advantageous embodiment is given by Claim 3:

Method according to claim 1, characterized in that a complexing agent is added to the halogenated oligosilane, said complexing agent being selected from a group comprising polyethers, crown ethers, and cryptands, preferably crown ethers, especially preferably 18-crown-6.

Complexing agents can bind a large number of metal ions, and in this way eliminate exchange with the desired product. For this purpose, the complex formation constant should be as high as possible, and the specific compound should not be too expensive. Here too, the complexing agent used should be easily removable during the planned separation process, and should not undergo undesired reactions with the OCS. Both conditions are met, for example, with crown ethers such as 18-crown-6.

A further advantageous embodiment is given by Claim 4:

Method according to claim 1, characterized in that to the halogenated oligosilane and/or fluoride is added before or during the processing phase a solvent that is selected from a group comprising alkanes, cycloalkanes, ethers, aromatics, and chlorinated silanes, preferably cycloalkanes and ethers such as triglyme, diglyme, dioxane, dibutyl ether, THF, and diethyl ether, especially preferably cycloalkanes, particularly cyclohexane, wherein the proportion of the solvent in the mixture with the halogenated oligosilanes is at least 0.01 mass %, preferably at least 0.1 mass %, especially preferably at least 1 mass %, especially at least 2 mass %.

The addition of solvents can be advantageous to deploy, for example, a solubilizing action. This particularly true with respect to the purifying additives that are used in the method according to the invention. The solvent used must thus be as inert and easily separable from the products as possible.

A further advantageous embodiment is given by Claim 5:

Method of claim 1, characterized in that X in $Si_nX_{2n+2}$ is more than 95 atom % chlorine, preferably more than 98 atom %, and/or the hydrogen content in $Si_nX_{2n+2}$ is less than 5 atom %, preferably less than 2 atom %, especially preferably less than 1 atom %.

The most important target compounds of the method of the present invention are highly chlorinated oligosilanes, wherein however also halogenated or partially hydrogenated OCSs can be implemented if they are present as liquid, or if liquefied, or in solution.

A further advantageous embodiment is given by Claim 6:

Method of claim 1, characterized in that the chlorinated oligosilane contains a diluent selected from a group comprising of $SiCl_4$, $Si_2Cl_6$, $Si_3Cl_8$, $Si_4Cl_{10}$, wherein the proportion of the diluent based on the halogenated oligosilane is least 0.001 mass %, preferably at least 0.1 mass %, especially preferably at least 1 mass %, especially at least 10 mass %.

The addition of diluents can then be advisable if the OCS is solid or too viscous to allow efficient processing.

In contrast to the above-mentioned solvents, diluents can also be used in large amounts if, as described, they are compounds that are chemically related to the OCS according to the invention and therefore do not introduce interfering contamination into the product.

A further advantageous embodiment is given by Claim 7:

Method of claim 1 characterized in that at least one separation process is operated at a pressure less than 1600 hPa, preferably less than 800 hPa, especially preferably less than 80 hPa, and especially less than 1 hPa.

Separation methods such as distillation, for example, should advantageously be carried out at reduced pressures to prevent decomposition phenomena in the presence of the purification agent. The higher the OCS in question boils, the lower the pressure must be to achieve a sufficient reduction in the boiling point.

A further advantageous embodiment is given by Claim 8:

Method according to claim 1, characterized in that the at least one processing step and/or one separation process is operated at a temperature of higher than 30° C., preferably higher than 50° C., especially preferably higher than 80° C., and especially higher than 100° C.

An increase in temperature is advantageous to achieve a faster reaction with the purification substances. It is furthermore useful for longer-chain OCSs to operate under heating to reduce the viscosity.

A further advantageous embodiment is given by Claim 9:

Method according to claim 1, characterized in that a content of 1 ppm each of Al, Fe, and Cu in the halogenated oligosilane will be reduced by purification to less than 100 ppb, preferably below 30 ppb, especially preferably below 5 ppb, and especially less than 1 ppb.

Without limiting the method according to the present invention thereby, typical metal content values before and after purification are indicated in this claim that are representative for a wide variety of metal contaminations.

A further advantageous embodiment is given by Claim 10:

Method according to claim 1, characterized in that to the halogenated oligosilane before or during the processing phase is added a siloxane as a pure compound or mixture of compounds preferably selected from the group $Cl_3SiOSiCl_3$, $Cl_3SiOSiCl_2SiCl_3$, $Cl_3SiOSiCl_2OSiCl_3$, wherein the proportion of the siloxane in the mixture with the halogenated oligosilane is at least 0.001 mass %, preferably at least 0.01 mass %, especially preferably at least 0.1 mass %, especially at least 1 mass %. The method according to the present invention provides here a further process variant in which halogenated disiloxane reactants are added to achieve a purification effect in the course of the overall process with regard to metal compounds and dopants such as boron and phosphorus. In this case, during the various process steps according to Claim 1, the disiloxanes bind a significant proportion of the metal and dopant contamination in the form of oxides or mixed oxides that, for example, contain Si—O groups, whereby this can be separated as low-volatility residues by the separation methods according to the present invention, for example, such as distillation.

The disiloxanes are advantageously mixed in at the beginning of the process, wherein these can, for example, be dissolved in $SiCl_4$ or be present as a liquid. The purification effect produced by these components can thereby be deployed from the first processing step, as provided according to the present invention. Specifically, however, the disiloxanes can also be added at a later point in time during the process according to the present invention, wherein a certain purification effect will continue to be deployed. As can readily be appreciated by one skilled in the art, the disclosed principle of the method will not be lost thereby.

The amount of the purification additive depends on the type and quantity of contaminants to be removed. A larger amount of disiloxane tends to lead to a better purification. However, depending on their vapor pressure, disiloxanes can also be carried over in the process and might interfere with the final product, which is why preferably they must be predominantly removed in the last step, e.g., by distillation. The less that is present from the outset, the better this will work, so that usually a compromise is chosen between the purification effect and tolerable residual content in the final product. Depending on the boiling point of the desired final product, it is advantageous to choose a disiloxane that has a boiling point that is as different as possible so as not to complicate the final purification step.

INDUSTRIAL APPLICABILITY

The method according to the present invention for purifying halogenated oligosilanes provides a significant economic advantage, since both the yield of products as well as the per-time yield can be significantly increased over the prior art by adding the additives according to the present invention.

Furthermore, the purity of the final products is increased by the addition of the purification agent according to the present invention, resulting in an improved market position for the product, thereby achieving a further economic advantage within a method for purifying chlorinated oligosilanes (OCSs).

Various solutions are possible for the technical implementation of the method, from which non-exclusive variants for solving the present problem are listed in the embodiments below.

Embodiment 1

70 kg hexachlorodisilane was treated with a suspension of 18 g 18-crown-6 and 2.7 g KF in 50 mL cyclohexane. The mixture was stirred for 2 h and then was fractionally distilled. A main run of 62 kg HCDS was obtained after 10 h. In the course of this purification, the original aluminum content of 3.8 ppm and iron content of 1.3 ppm were thus respectively reduced to below 30 ppb.

Embodiment 2

60 kg hexachlorodisilane was treated with a suspension of 50 g 18-crown-6 and 5 g KF in 150 mL triglyme. The mixture was stirred overnight and then was fractionally distilled. A main run of 45 kg HCDS was obtained after 9 h. In the course of this purification, the original aluminum content of 800 ppb, iron content of 75 ppb, and magnesium content of 180 ppb were thus respectively reduced to below 5 ppb.

Embodiment 3

8 kg octachlorotrisilane was treated with a suspension of 0.5 g NaF and 4.5 g 15-crown-5 in 30 mL dichloromethane. The mixture was stirred at rt overnight and then was decanted from the undissolved solids. The OCTS was then quickly distilled off under vacuum (approx. 10 hPa) through a short column, and was then fractionally distilled under vacuum (approx. 10 hPa) A main run of 5 kg OCTS was obtained over 8 h. The content values in ppb for the exemplary trace contaminants before and after purification are shown in the following table.

| OCTS | Al | Cr | Mn | Cu | Fe | Mg | K | Na | Ti | Ca |
|---|---|---|---|---|---|---|---|---|---|---|
| Crude | 920 | <30 | <30 | 58 | 46 | 110 | 160 | 120 | <30 | 750 |
| Purified | <30 | <30 | <30 | <30 | <30 | <30 | <50 | <50 | <30 | <50 |

Embodiment 4

1.5 kg of a mixture of approx. 90% of a tetrachlorodisilane isomer mixture and 10% pentachlorodisilane was treated with a suspension of 0.1 g NaF and 1 g 12-crown-4 in 20 mL dichloromethane. The mixture was stirred at rt for 2 h and then overnight at 0° C. The liquid phase was decanted from the undissolved solids, filtered through a fritted glass filter (D3), and then rapidly recondensed through a short column under vacuum (approx. 10 hPa). The condensate was then fractionally distilled under vacuum (approx. 10 hPa). A main run of 1.2 kg oligosilane mixture was obtained over 14 h. The content values in ppb for the exemplary trace contaminants before and after purification are shown in the following table.

| TCDS/PCDS | Al | Cr | Mn | Cu | Fe | Mg | K | Na | Ti | Ca |
|---|---|---|---|---|---|---|---|---|---|---|
| Purified | <30 | <30 | <30 | <30 | <30 | <30 | <50 | <50 | <30 | <50 |

Embodiment 5

35 kg hexachlorodisilane was treated with a suspension of 3 g KF, 12 g 15-crown-5 and 15 g 18-crown-6 in 120 mL dichloromethane. The mixture was heated to reflux for approx. 2 h, and then was fractionally distilled. A main run of 28 kg HCDS was obtained over 8 h.

The content values in ppb for the exemplary trace contaminants before and after purification are shown in the following table.

| HCDS | Al | B | Sb | Cu | Fe | Mg | K | Na | Ti | Ca |
|---|---|---|---|---|---|---|---|---|---|---|
| Crude | 112 | 420 | 0.7 | 5.2 | 848 | 11 | 78 | 49 | 734 | 125 |
| Purified | 25 | 23 | 0.1 | 0.8 | 13 | 7 | 6.6 | 2.2 | 27 | 26 |

Embodiment 6

40 kg hexachlorodisilane was treated with a suspension of 3.5 g KF, 14 g 15-crown-5 and 17 g 18-crown-6 in 140 mL dichloromethane. The mixture was heated to reflux for approx. 2 h, and then was fractionally distilled. A main run of 32 kg HCDS was obtained over 10 h. From this, 26 kg HCDS was treated with a suspension of 2.2 g KF, 11 g 18-crown-6, and 10 g 12-crown-4 in 100 mL dichloromethane, and then again fractionally distilled. A main run of 20 kg HCDS was obtained after 9 h. The content values in ppb for the exemplary trace contaminants before and after purification are shown in the following table.

| HCDS | Al | B | Sb | Cu | Fe | Mg | K | Na | Ti | Ca |
|---|---|---|---|---|---|---|---|---|---|---|
| Crude | 55 | 57 | 0.9 | 4.5 | 21 | 8.1 | 39 | 133 | 342 | 77 |
| Purified | 3.5 | 2.4 | 0.1 | 0.1 | 1.6 | 0.8 | 0.07 | 0.9 | 2.8 | 6.5 |

The invention claimed is:

1. A method for purification of halogenated oligosilanes $Si_nX_{2n+2}$ with n=2 through n=6 as compounds or as mixtures of compounds in which the substituents X comprise chlorine or chlorine and hydrogen, the process comprises the steps:
   (a) adding a complexing agent and a fluoride or fluoride mixture to the halogenated oligosilane, wherein fluoride $F^-$ from the fluoride or fluoride mixture is made available for a reaction in an amount of more than 1 ppb calculated as $F^-$ in relation to the mass of the halogenated oligosilane,
   b) carrying out at least one processing step in which at least the fluoride acts upon the halogenated oligosilane, wherein the at least one processing step is selected from the group consisting of stirring, swirling, shaking, heating to reflux, and diffusing, wherein a solvent is added to the halogenated oligosilane and/or fluoride before or during the processing step, the solvent is selected from the group consisting of alkanes, cycloalkanes, ethers, aromatics, and chlorinated silanes, wherein the proportion of the solvent in the mixture with the halogenated oligosilanes is at least 0.01 mass % and wherein a siloxane as a pure compound or mixture of compounds selected from the group consisting of $Cl_3SiOSiCl_3$, $Cl_3SiOSiCl_2SiCl_3$, and $Cl_3SiOSiCl_2OSiCl_3$ is added to the halogenated oligosilane before or during the processing step, wherein the proportion of the siloxane in the mixture with the halogenated oligosilane is at least 0.001 mass %, and
   (c) carrying out at least one separation method for the isolation of the halogenated oligosilane, wherein the separation method is selected from the group consisting of decanting, filtering, distilling, and subliming.

2. The method according to claim 1, wherein the fluoride is selected from the group consisting of alkali metal fluorides, alkaline earth metal fluorides, silicon fluorides $Si_nY_oF_p$, with Y=halogen, organyl, siloxanyl and/or hydrogen; o+p=2n+2; n >1, and zinc fluoride.

3. The method according to claim 1, wherein the complexing agent is being selected from the group consisting of polyethers, crown ethers, and cryptands.

4. The method according to claim 1, wherein X in $Si_nX_{2n+2}$ is more than 95 atom % chlorine, and/or the hydrogen content in $Si_nX_{2n+2}$ is less than 5 atom %.

5. The method according to claim 1, wherein the chlorinated oligosilane contains a diluent selected from the group consisting of $SiCl_4$, $Si_2Cl_6$, $Si_3Cl_8$, and $Si_4Cl_{10}$, wherein the proportion of the diluent based on the halogenated oligosilane is least 0.001 mass %.

6. The method according to claim 1, wherein at least one separation method is operated at a pressure of less than 1600 hPa.

7. The method according to claim 1, wherein the at least one processing step and/or one separation method is operated at a temperature of higher than 30° C.

8. A method for the purification of halogenated oligosilanes $Si_nX_{2n+2}$ with n=2 through n=6 as compounds or as mixtures of compounds in which the substituents X comprise chlorine or chlorine and hydrogen, the process comprises the steps:
   (a) adding a complexing agent and a fluoride or fluoride mixture to the halogenated oligosilane, wherein fluoride $F^-$ from the fluoride or fluoride mixture is made available for a reaction in an amount of more than 1 ppb calculated as $F^-$ in relation to the mass of the halogenated oligosilane,
   (b) carrying out at least one processing step in which at least the fluoride acts upon the halogenated oligosilane, wherein the at least one processing step is selected from the group consisting of stirring, swirling, shaking, heating to reflux, and diffusing, and
   (c) carrying out at least one separation method for the isolation of the halogenated oligosilane takes place, wherein the separation method is selected from the group consisting of decanting, filtering, distilling, and subliming.

9. The method according to claim 8, wherein the fluoride is selected from the group consisting of alkali metal fluorides, alkaline earth metal fluorides, silicon fluorides $Si_nY_oF_p$, with Y=halogen, organyl, siloxanyl and/or hydrogen; o+p=2n+2; n >1.

10. The method according to claim 8, wherein said complexing agent being selected from the group consisting of polyethers, crown ethers, and cryptands.

11. The method according to claim 8, wherein a solvent is added to the halogenated oligosilane and/or the fluoride before or during the processing step, wherein the solvent is selected from the group consisting of alkanes, cycloalkanes, ethers, aromatics, and chlorinated silanes, wherein the proportion of the solvent in the mixture with the halogenated oligosilanes is at least 0.01 mass %.

12. The method of claim 8, wherein X in $Si_nX_{2n+2}$ is more than 95 atom % chlorine, and/or the hydrogen content in $Si_nX_{2n+2}$ is less than 5 atomic %.

13. The method of claim 8, wherein the chlorinated oligosilane contains a diluent selected from the group consisting of $SiCl_4$, $Si_2Cl_6$, $Si_3Cl_8$, and $Si_4Cl_{10}$, wherein the proportion of the diluent based on the halogenated oligosilane is least 0.001 mass %.

14. The method of claim 8, wherein at least one separation method is operated at a pressure of less than 1600 hPa.

15. The method according to claim 8, wherein the at least one processing step and/or one separation method is operated at a temperature of higher than 30° C.

16. The method according to claim 8, that wherein a siloxane as a compound or a mixture of compounds selected from the group consisting of $Cl_3SiOSiCl_3$, $Cl_3SiOSiCl_2SiCl_3$, and $Cl_3SiOSiCl_2OSiCl_3$ is added to the halogenated oligosilane before or during the processing step, wherein the proportion of the siloxane in the mixture with the halogenated oligosilane is at least 0.001 mass %.

* * * * *